United States Patent
Abraham et al.

(10) Patent No.: US 12,070,421 B2
(45) Date of Patent: Aug. 27, 2024

(54) AUTOMATED FINE ADJUSTMENT OF AN OPHTHALMIC SURGERY SUPPORT

(71) Applicant: Alcon Inc., Fribourg (CH)

(72) Inventors: Mario Abraham, Burgthann (DE); Michael Wittnebel, Hirschaid (DE)

(73) Assignee: ALCON INC., Fribourg (CH)

( * ) Notice: Subject to any disclaimer, the term of this patent is extended or adjusted under 35 U.S.C. 154(b) by 305 days.

(21) Appl. No.: 16/333,956

(22) PCT Filed: Oct. 19, 2016

(86) PCT No.: PCT/IB2016/056299
§ 371 (c)(1),
(2) Date: Mar. 15, 2019

(87) PCT Pub. No.: WO2018/073624
PCT Pub. Date: Apr. 26, 2018

(65) Prior Publication Data
US 2019/0231594 A1 Aug. 1, 2019

(51) Int. Cl.
*A61F 9/008* (2006.01)
*A61F 9/007* (2006.01)
(Continued)

(52) U.S. Cl.
CPC .......... *A61F 9/00802* (2013.01); *A61F 9/007* (2013.01); *G02B 27/0093* (2013.01);
(Continued)

(58) Field of Classification Search
CPC .............................................. A61F 2009/00846
See application file for complete search history.

(56) References Cited

U.S. PATENT DOCUMENTS 6,280,436 B1 8/2001 Freeman et al.
6,607,527 B1 8/2003 Ruiz
(Continued)

FOREIGN PATENT DOCUMENTS

CA 2729721 C 8/2015
JP 2003506139 A 2/2003
(Continued)

OTHER PUBLICATIONS

Nayak, D. P. (Mar. 1, 2015). Lasik surgery—things to keep in mind before undergoing one. TheHealthSite. https://www.thehealthsite.com/diseases-conditions/lasik-surgery-things-to-keep-in-mind-before-undergoing-one-412/ (Year: 2015).*

*Primary Examiner* — Lynsey C Eiseman
*Assistant Examiner* — Skylar Lindsey Christianson (57) ABSTRACT

The present disclosure provides a system for automated fine adjustment of an ophthalmic surgery support in which an eye tracking system detects a detectable position of an eye. The direction and distance the support must be adjusted for the eye to be centered may be determined based on the detectable position. A control signal is generated and transmitted to a control device that adjusts the position of the support to center the eye. The disclosure further provides a method for automated fine adjustment of a support, which includes detecting a detectable position of an eye, determining whether the eye is centered in relation to the center of the detection field of an eye tracking system based on the detectable position, determining a direction and a distance the detectable position must be adjusted to be centered, and generating and transmitting a control signal to adjust the position of the support.

13 Claims, 4 Drawing Sheets

(51) Int. Cl.
  *G02B 27/00* (2006.01)
  *G06T 7/70* (2017.01)
  *A61F 9/00* (2006.01)

(52) U.S. Cl.
  CPC ........ *G06T 7/70* (2017.01); *A61F 2009/0035* (2013.01); *A61F 2009/00846* (2013.01); *G06T 2207/30041* (2013.01)

(56) References Cited

U.S. PATENT DOCUMENTS

| | | | |
|---|---|---|---|
| 2002/0036749 A1 | 3/2002 | Isogai | |
| 2002/0051116 A1* | 5/2002 | Van Saarloos | G06T 7/73 351/204 |
| 2004/0143246 A1* | 7/2004 | Maeda | A61F 9/008 606/5 |
| 2008/0278687 A1* | 11/2008 | Somani | A61F 9/00806 351/208 |
| 2009/0093798 A1* | 4/2009 | Charles | A61F 9/00823 606/4 |
| 2009/0247997 A1* | 10/2009 | Watanabe | A61F 9/00836 606/4 |
| 2011/0040292 A1* | 2/2011 | Riedel | A61F 9/00802 606/5 |
| 2011/0276042 A1 | 11/2011 | Dick | |
| 2012/0078240 A1* | 3/2012 | Spooner | A61F 9/00827 606/17 |
| 2015/0141972 A1 | 5/2015 | Woodley et al. | |
| 2017/0020627 A1* | 1/2017 | Tesar | A61B 1/0005 |

FOREIGN PATENT DOCUMENTS

| | | | |
|---|---|---|---|
| JP | 2016520362 A | 7/2016 | |
| WO | 2005/011544 A1 | 2/2005 | |
| WO | WO-2005011544 A1 * | 2/2005 | ........ A61F 9/00814 |

* cited by examiner

AUTOMATED FINE ADJUSTMENT OF AN OPHTHALMIC SURGERY SUPPORT

TECHNICAL FIELD

The present disclosure relates to ophthalmic surgery and surgical equipment, and more specifically, to systems and methods for automated fine adjustment of a support.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is surgery performed on the eye or any part of the eye. Ophthalmic surgery is regularly performed to repair retinal defects, repair eye muscles, remove cataracts or cancer, or to restore or improve vision. Refractive eye surgery, for example, is a type of ophthalmic surgery used to improve the refractive state of the eye for the purpose of decreasing or eliminating dependency on glasses or contact lenses. Refractive surgery procedures may include surgically remodeling the cornea and may be performed by lasers.

In refractive surgery and various other ophthalmic surgical procedures, ablation may be performed, which is the use of a laser to remove tissue. When performing ophthalmic surgery with lasers, an eye tracking system is often used to assist in centering the laser or otherwise controlling its position, monitoring the position of the eye, and maintaining the eye in an acceptable position throughout the procedure. Throughout an ophthalmic surgical procedure, the patient is positioned on a support.

SUMMARY

The present disclosure provides a system for automated fine adjustment of an ophthalmic surgery support. The system includes a support, a control device operable to control a position of the support, an eye tracking system operable to detect a detectable position of an eye and generate data relating to the detectable position, a processing system comprising at least one programmed processing device, the processing system operable to receive data from the eye tracking system relating to the detectable position, determine a detectable position of the eye in relation to a center of a detection field of the eye tracking system, determine a direction and a distance the detectable position of the eye must be adjusted to be centered in relation to the center of the detection field of the eye tracking system, generate a control signal operable to adjust the position of the support so that the eye is centered in relation to the center of the detection field of the eye tracking system, and transmit the control signal to the control device to adjust the position of the support.

In additional embodiments, which may be combined with one another unless clearly exclusive: the support is a couch or a bed; a device for manual confirmation of an adjustment operable to input a confirmation is a switch, a key or a joystick; adjusting the position of the support so that the eye is centered in relation to the center of the detection field of the eye tracking system is performed automatically, without manual confirmation or automatically but only after manual confirmation; and adjusting the position of the support is performed during initialization of the eye tracking system, during surgery, during equipment calibration, during equipment calibration including automated fine adjustment of test targets, or during a docking procedure of a suction cone for a femtosecond laser surgery.

The present disclosure further provides a method for automated fine adjustment of a support. The method includes detecting a detectable position of an eye, generating data relating to the detectable position, processing data relating to the detectable position, determining a detectable position of the eye in relation to a center of a detection field of an eye tracking system, determining a direction and a distance the detectable position of the eye must be adjusted to be centered in relation to the center of the detection field of the eye tracking system, generating a control signal operable to adjust an ophthalmic surgery support so that the eye is centered in relation to the center of the detection field of the eye tracking system, and transmitting the control signal to a control device operable to adjust a position of the ophthalmic surgery support.

In additional embodiments, which may be combined with one another unless clearly exclusive: the support is a couch or a bed; adjusting a position of an ophthalmic surgery support so that the eye is centered in relation to the center of the detection field of the eye tracking system is performed automatically, without manual confirmation, or automatically but only after manual confirmation; and adjusting the position of the support is performed during initialization of the eye tracking system, during surgery, during equipment calibration, during equipment calibration including automated fine adjustment of test targets, or during a docking procedure of a suction cone for a femtosecond laser surgery.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure provides systems and methods for automated fine adjustment of a support used in ophthalmic surgery. During ophthalmic surgery, a patient is positioned on a support, for example, a couch or bed. An eye tracking system is used to determine the position of the eye, monitor the position of the eye, and assist in maintaining the eye in an acceptable position throughout the surgical procedure. Primary tracking operations are first used to determine the position of the eye to determine whether the eye is centered in relation to the detection field of the eye tracking system. Once centered, secondary tracking operations may be initialized to monitor the position of the eye throughout the duration of the procedure.

Before secondary tracking operations can be initialized to monitor the position of the eye throughout the procedure, the eye tracking system should first be centered. The eye tracking system may be centered in relation to any point of the eye, for example, the cornea or other structure of interest. If the eye is not centered prior to secondary eye tracking system initialization, this can cause interference that affects further tracking. Such interference may lead to undesirable offsets and rotations that can result in errors in ablation and other higher-order aberrations. The present disclosure provides systems and methods for automated fine adjustment of the support to center the eye in relation to the center of the detection field of the eye tracking system.

To perform automated fine adjustment, the systems of the present disclosure provide a support, a control device to adjust the position of the support, an eye tracking system, and a processing system that receives data from the eye tracking system, determines a position of the eye in relation to a center of the detection field of the eye tracking system, generates a control signal for adjusting the position of the support so that the eye is centered in relation to the center of the detection field of the eye tracking system, and transmits the control signal to the control device to adjust the position of the support. Because any camera of an eye tracking system may be focused at any possible distance by adjusting or replacing optical elements of the camera, such as lenses, automated fine adjustment may be performed without the eye being first positioned at a threshold distance.

The systems and methods of the present disclosure provide the user many benefits. For instance, ophthalmic laser surgery implementing such systems and methods is more reliable because treatment errors due to improper eye alignment can be minimized and because automated adjustment is faster than manual adjustment. Automated fine adjustment systems can position the patient more accurately than manual adjustment because such systems can detect a target location more precisely than a user can. Automated adjustment is also more accurate and more precise because objective data for the eye is available, at least in the X-Y plane of the detectable range. The X-Y plane is defined as the plane roughly perpendicular to the apex of the cornea. A defined offset may be implemented to initiate eye tracking beginning from a defined position offset from the cornea or other specified starting position. Automated fine adjustment may also be used for equipment calibration, such as calibration using test targets, and in docking a suction cone for femtosecond laser ophthalmic surgery.

Figure 1:
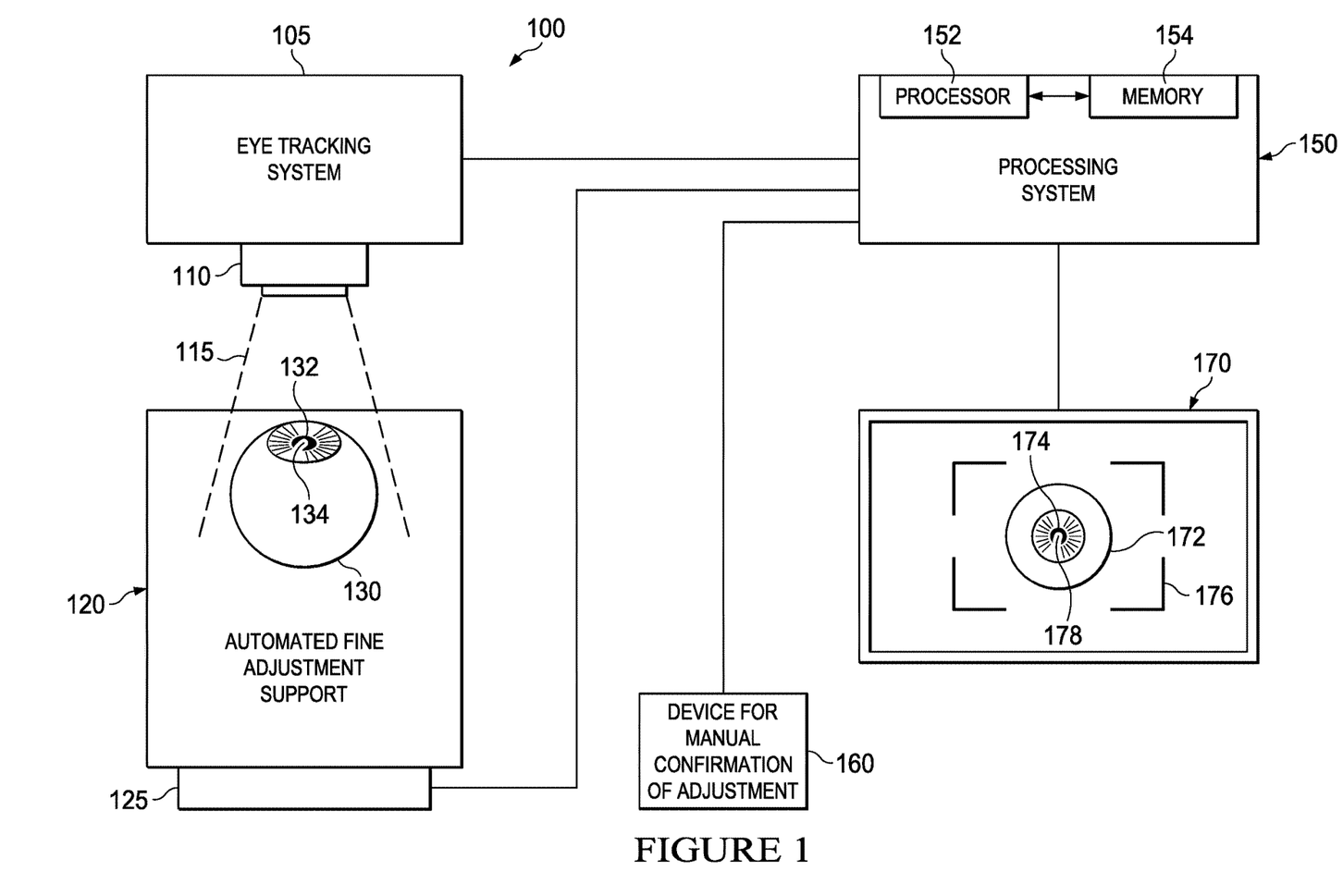
FIG. 1 is a schematic representation of elements of a surgical system for automated fine adjustment of an ophthalmic surgery support.

Referring now to the drawings, FIG. 1 is a schematic representation of elements of a system 100 for automated fine adjustment of an ophthalmic surgery support. System 100 includes support 120 connected to control device 125, operable to adjust the position of the support, eye tracking system 105, and processing system 150. During ophthalmic surgery, a patient is placed on support 120. Eye tracking system 105 includes at least one camera 110 operable to detect a detectable position of the eye 130 and generate data relating to the detectable position. The camera may include an autofocus feature. Eye tracking system 105 transmits data relating to the detectable position to processing system 150. Processing system 150 processes the data relating to the detectable position to determine the position of the eye and whether the eye is centered in relation to the center of the detection field 115 of the eye tracking system.

Any point of the eye 132 may be specified as the point to be centered in relation to the center of the detection field. For instance, the center-point of the pupil 134 or any other structure of interest. Defined offsets may also be specified to cause tracking operations to be initialized from a defined offset in relation to the point of centering. System 100 may further include a device for manual confirmation of an adjustment 160 and display 170. Device for manual confirmation 160 may be any device that can input a confirmation, for example, a button, switch, key or joystick. Device for manual confirmation 160 may also be a contactless device that can input a confirmation, for example, by voice recognition or gesture control.

Processing system 150 is connected to other system components, wirelessly or through a wired connection, which include eye tracking system 105 and control device 125, and in certain embodiments, a device for manual confirmation of adjustment 160 and a display 170.

As shown in FIG. 1, processing system 150 receives data from eye tracking system 105 relating to the detectable position of the eye 132, and processes the data to determine whether center-point of the pupil 134 is centered in relation to field of detection 115. If the center-point of the pupil 134 is not centered in relation to field of detection 115, processing system 150 determines the direction and distance support 120 must be adjusted for center-point of the pupil 134 to be centered. Processing system 150 generates and transmits a control signal for automated fine adjustment to control device 125, in which the control signal indicates the direction and distance to adjust the support. System 100 may be configured to require manual confirmation of an adjustment to be input via device 160 before automated fine adjustment is performed. For example, if the system is configured to require manual confirmation, the control device will not adjust the support until manual confirmation is input. In another example, if the system is configured not to require manual confirmation, the control device will automatically adjust the support without any manual confirmation. In this example, the control device may adjust the support continuously throughout the procedure, as needed, based on the determinations of processing system 150. This ability may be particularly useful in compensating for patient movement.

Processing system 150 may also generate a pictorial representation based on data received relating to the detectable position of the eye. The pictorial representation may be transmitted to display 170 to be presented as an image during ophthalmic surgery. The image may include, for example, the position of the eye 172, the center of the pupil 174, the field of detection 176 of eye tracking system 105, and the center 178 of the field of detection 176. The image may further include an indication of whether center of the pupil 174 is centered in relation to center 178 of field of detection 176. To indicate whether center of the pupil 174 is centered, the image may include colored graphics, for example, green graphics to indicate the pupil is centered and orange graphics to indicate the pupil is not centered. Display 170 may further indicate whether automated fine adjustment is required to cause center of the pupil 174 to be centered. If the system is configured to require manual adjustment, the image may further include an indication that an adjustment is pending manual confirmation, including the direction and distance determined for the adjustment. If the system is not configured to require manual adjustment, the image may further include an indication that an adjustment was performed or is about to be performed, including the direction and distance determined for the adjustment.

A processor 152 of processing system 150 may comprise, for example a microprocessor, microcontroller, digital signal processor (DSP), application specific integrated circuit (ASIC), or any other digital or analog circuitry configured to interpret and/or execute program instructions and/or process data. In some embodiments, processor 152 may interpret and/or execute program instructions and/or process data stored in memory 154. Memory 154 may be configured in part or whole as application memory, system memory, or both. Memory 154 may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

Figure 2:
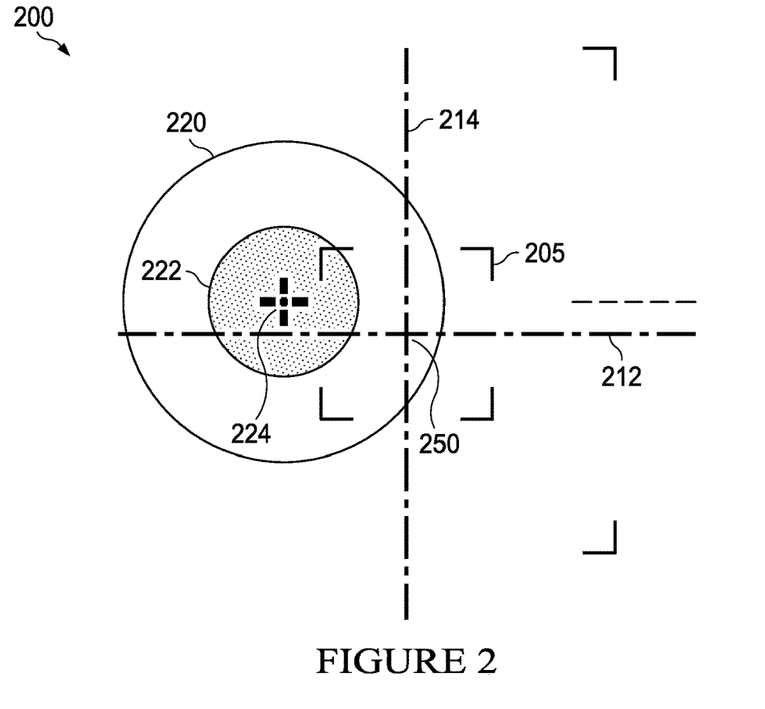
FIG. 2 is a digitally processed image of a pupil that is off center in relation to the center of the detection field of an eye tracking system.
Figure 3:
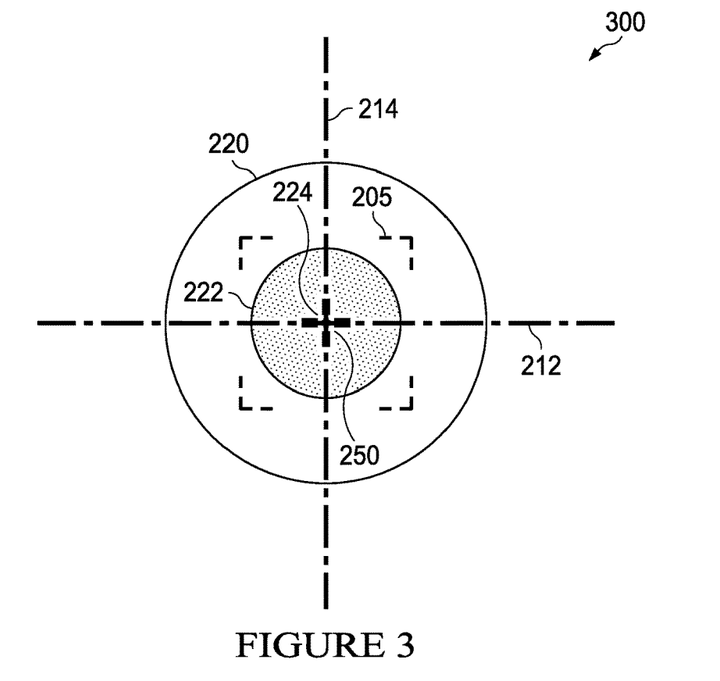
FIG. 3 is a digitally processed image of a pupil that is centered in relation to the center of the detection field of an eye tracking system.

FIG. 2 is a digitally processed image 200 of a pupil 222 of an eye 220 that is off center in relation to the center of the detection field of eye tracking system 250, and requires further adjustment to be centered. To assist in centering the pupil, the image shown in FIG. 2 presents a graphic indicating the valid range for centering 205. The valid range for centering 205 may be visually represented by a square. The square may be colored to indicate that the eye is not yet centered, for example, an orange square. As shown in FIG. 2, the square may also be illustrated with solid lines to indicate that the eye is not centered. In contrast, the square may be illustrated with dotted lines to indicate that the eye is centered, as shown in FIG. 3. To assist in centering, the image further indicates X-axis 212 and Y-axis 214, defined in relation to the x-y plane roughly perpendicular to the apex of the cornea. It is important to center the pupil with the center of the detection field of the eye tracking system 250 before initialization of further tracking operations because the accuracy of subsequent tracking operations relies upon the starting point being correctly centered. In FIG. 2, center of the pupil 224 should be adjusted to be centered in relation to center of detection field 250.

FIG. 3 is a digitally processed image 300 of a pupil 222 of an eye 220 that is centered in relation to the center of the detection field of the eye tracking system 250, and does not require further adjustment to be centered. To assist in centering the pupil, the image shown in FIG. 3 presents a graphic indicating the valid range for centering 205. The valid range for centering 205 may be visually represented by a square. The square may be colored to indicate that the eye is not yet centered, for example, a green square. As shown in FIG. 3, the square may also be illustrated with dotted lines to indicate that the eye is centered. To assist in centering, the image further indicates X-axis 212 and Y-axis 214, defined in relation to the x-y plane roughly perpendicular to the apex of the cornea. It is important to center the pupil with the center of the detection field of the eye tracking system 250 before initialization of further tracking operations because the accuracy of subsequent tracking operations relies upon the starting point being correctly centered. In FIG. 3, center of the pupil 224 does not require further adjustment to be centered in relation to center of detection field 250.

Figure 4:
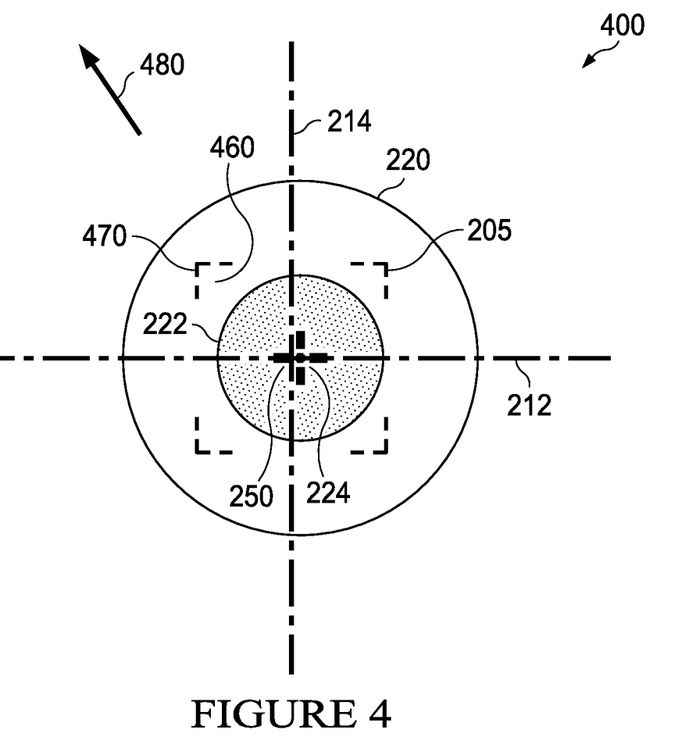
FIG. 4 is a digitally processed image of a pupil in a valid range for centering in relation to the center of the detection field of an eye tracking system; the pupil may be positioned closer to the actual center of the detection field by automated fine adjustment of an ophthalmic surgery support.

FIG. 4 is a digitally processed image 400 of a pupil 224 in a valid range for centering 205, in relation to the center of the detection field of the eye tracking system; but, the image illustrates that the pupil could be positioned closer to the actual center of the detection field by implementing automated fine adjustment of the support. The valid range for centering 205 may be visually represented by a square. The square may be colored to indicate that the eye is centered. The square may also be illustrated with dotted lines to indicate that the eye is centered. In FIG. 4, for example, the square is illustrated with dotted lines, indicating that the center of pupil 224 is within valid range for centering 205. However, the center of pupil 224 is still not centered in relation to the center of the detection field of the eye tracking system 250. To assist in centering, the image further indicates X-axis 212 and Y-axis 214, defined in relation to the x-y plane roughly perpendicular to the apex of the cornea. Centering error 460 is shown in the top left corner of the valid range for centering 205. Automated fine adjustment can be used to correct error 460 by adjusting pupil 224 in direction 480 until it reaches ideal position 470.

Figure 5:
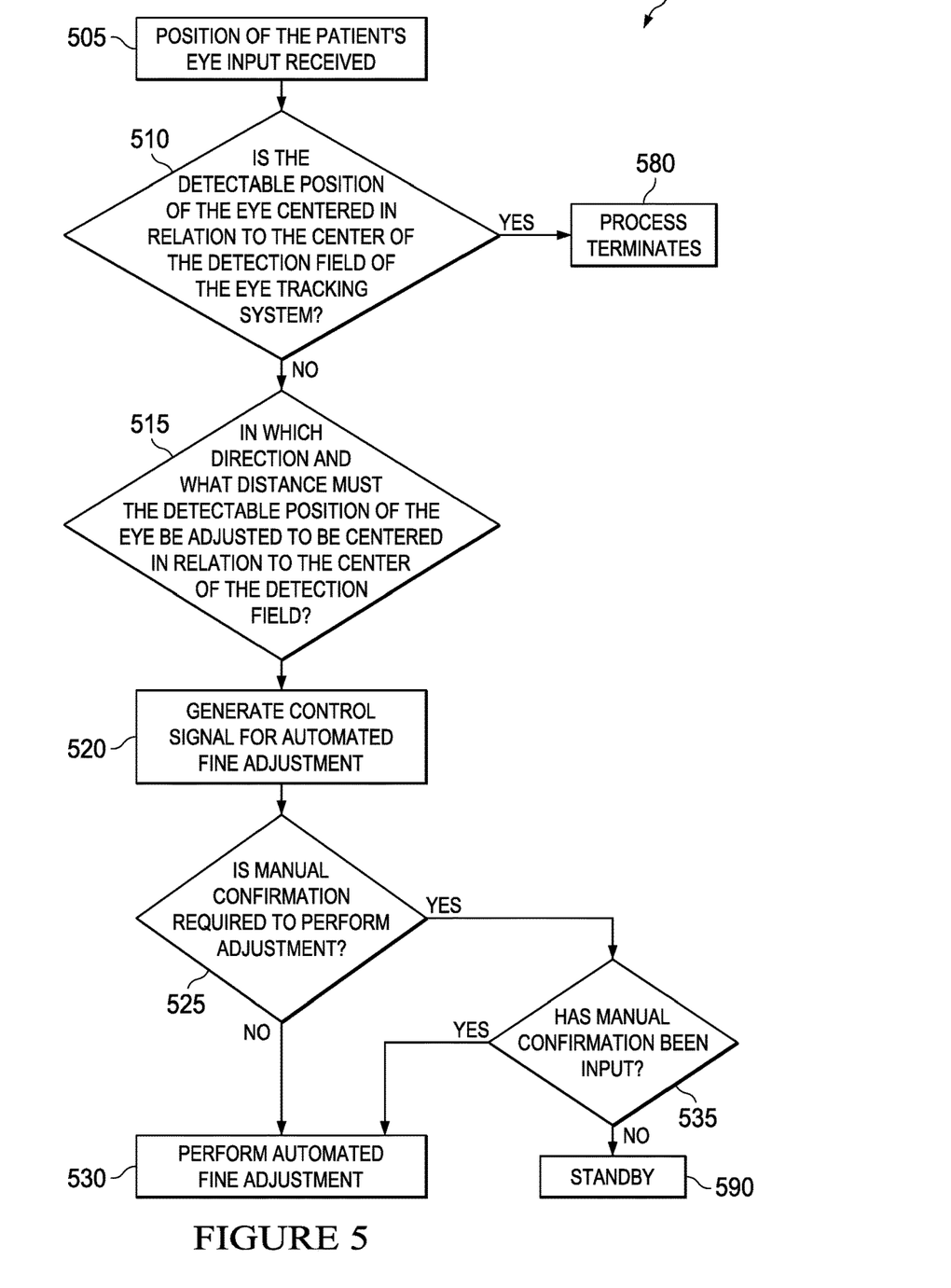
FIG. 5 is a flow chart of a method for performing automated fine adjustment of a ophthalmic surgery support.

FIG. 5 is a flow chart of a method 500 for performing automated fine adjustment of an ophthalmic surgery support. At step 505, an input is received by a processor with a memory, wherein the input indicates a position of an eye. At step 510, the position of the eye is evaluated to determine if the eye is centered in relation to the center of the detection field of the eye tracking system. If the eye is centered in relation to the center of the detection field of the eye tracking system, then at 580, the automated fine adjustment process terminates. If the eye is not centered in relation to the center of the detection field of the eye tracking system, then at 515, the direction and distance the eye must be adjusted to be centered in relation to the center of the detection field of the eye tracking system may be determined.

At step 520, a control signal is generated for automated fine adjustment, the control signal indicating the distance and direction the eye may be adjusted to be centered in relation to the center of the detection field of the eye tracking system. At step 525, whether manual confirmation is required to perform automated fine adjustment is determined. If manual confirmation is not required, then at 530, automated fine adjustment may be performed automatically, without manual confirmation. If manual confirmation is required, then at 535, whether manual confirmation has been input may be determined. If manual confirmation has been input, then at 530, automated fine adjustment may be performed automatically, without manual confirmation. But, if manual confirmation has not yet been input, then at 590, the control signal generated may be kept on standby and automated fine adjustment will not be performed until manual confirmation is input. At step 590, the control signal generated may be kept on standby prior to or after being transmitted to the control device of the support.

The patient may be positioned within a detection range of the eye tracking system before any steps of the method are performed, and a warning may be generated if the patient is not within the detection range at the beginning of performance of the method or if the patient moves out of the detection range during performance of the method.

Method 500 may be implemented using the system of FIG. 1, or any other suitable system. The preferred initialization point for such methods and the order of their steps may depend on the implementation chosen. In some embodiments, some steps may be optionally omitted, repeated, or combined. In some embodiments, some steps of such methods may be executed in parallel with other steps. In certain embodiments, the methods may be implemented partially or fully in software embodied in computer-readable media.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such wires, optical fibers, and other electromagnetic and/or optical carriers; and/or any combination of the foregoing.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for automated fine adjustment of an ophthalmic surgery support comprising:
   a support, the support configured to hold a patient, the patient having an eye;
   a control device operable to control a position of the support;
   an eye tracking system comprising a camera operable to detect a detectable position of the eye and generate data relating to the detectable position during primary tracking operations;
   a display operable to present an image;
   a device for manual confirmation of an adjustment, the device operable to input a manual confirmation;
   a processing system comprising at least one programmed processing device, the processing system operable to:
      receive data from the eye tracking system relating to the detectable position;
      determine the detectable position of the eye in relation to a center of a detection field of the eye tracking system;
      determine a direction and a distance the detectable position of the eye must be adjusted in an x-y plane to be centered in relation to the center of the detection field of the eye tracking system, the x-y plane approximately perpendicular to an apex of a cornea of the eye;
      generate a pictorial representation for the image that includes the direction and the distance determined to adjust the position of the support in the x-y plane and that includes a graphic indicating a valid range for centering the eye relative to the detection field of the eye tracking system, the image including an indication that the adjustment of the position of the support is pending manual confirmation;
      transmit the pictorial representation to the display to present the image, the image including the direction and the distance determined to adjust the position of the support in the x-y plane, the graphic indicating the valid range for centering the eye relative to the detection field of the eye tracking system, and the indication that the adjustment of the position of the support is pending manual confirmation;
      in response to the manual confirmation, generate a control signal operable to adjust the position of the support so that the detectable position of the eye is centered in relation to the center of the detection field of the eye tracking system; and
      transmit the control signal to the control device to adjust the position of the support.

2. The system of claim 1, wherein adjusting the position of the support is performed during initialization of the eye tracking system.

3. The system of claim 1, wherein the device for manual confirmation of an adjustment is a button, a switch, a key, a joystick, or by voice recognition or gesture control.

4. The system of claim 1 wherein the image further comprises a graphic indicating a centering error.

5. The system of claim 4, wherein:
   the graphic is a first color when the eye is not centered; and
   the graphic is a second color when the eye is centered.

6. The system of claim 1 wherein the processing system is further configured to generate a warning if a patient is not within the detection range or if the patient moves out of the detection range.

7. The system of claim 1, wherein the graphic indicating the valid range for centering comprises a square.

8. A method for automated fine adjustment of a support comprising:
   detecting a detectable position of an eye;
   generating data relating to the detectable position;
   processing data relating to the detectable position;
   determining the detectable position of the eye in relation to a center of a detection field of an eye tracking system during primary tracking operations;
   determining a direction and a distance the detectable position of the eye must be adjusted in an x-y plane to be centered in relation to the center of the detection field of the eye tracking system, the x-y plane approximately perpendicular to an apex of a cornea of the eye;
   generating a pictorial representation for an image that includes the direction and the distance determined to adjust the position of the support in the x-y plane and that includes a graphic indicating a valid range for centering the eye relative to the detection field of the eye tracking system, the image including an indication that the adjustment of the position of the support is pending manual confirmation;
   transmitting the pictorial representation to a display to present the image, the image including the direction and the distance determined to adjust the position of the support in the x-y plane, the graphic indicating the valid range for centering the eye relative to the detection field of the eye tracking system, and the indication that the adjustment of the position of the support is pending manual confirmation;
   in response to the manual confirmation, generating a control signal operable to adjust an ophthalmic surgery support, the ophthalmic surgery support configured to hold the eye, so that the detectable position of the eye is centered in relation to the center of the detection field of the eye tracking system; and transmitting the control signal to a control device operable to adjust a position of the ophthalmic surgery support.

9. The method of claim 8, wherein automated fine adjustment of the support is performed during initialization of the eye tracking system.

10. The method of claim 8 wherein the image further comprises a graphic indicating a centering error.

11. The method of claim 10, wherein:
the graphic is a first color when the eye is not centered; and
the graphic is a second color when the eye is centered.

12. The method of claim 8 further comprising:
generating a warning if a patient is not within the detection range or if the patient moves out of the detection range.

13. The method of claim 8, wherein the graphic indicating the valid range for centering comprises a square.

* * * * *